(12) United States Patent
Toussaint

(10) Patent No.: US 7,757,693 B2
(45) Date of Patent: Jul. 20, 2010

(54) CONTINUOUSLY ADJUSTABLE MANDIBULAR PROTRUSION SPLINT FOR TREATING SNORING AND OBSTRUCTIVE SLEEP APNEA

(76) Inventor: Winfried Toussaint, Finkenweg 17, Bensheim (DE) 64625

( * ) Notice: Subject to any disclaimer, the term of this patent is extended or adjusted under 35 U.S.C. 154(b) by 513 days.

(21) Appl. No.: 11/719,680

(22) PCT Filed: Nov. 23, 2005

(86) PCT No.: PCT/DE2005/002095

§ 371 (c)(1),
(2), (4) Date: May 18, 2007

(87) PCT Pub. No.: WO2006/058514

PCT Pub. Date: Jun. 8, 2006

(65) Prior Publication Data

US 2009/0090371 A1    Apr. 9, 2009

(30) Foreign Application Priority Data

Dec. 1, 2004    (DE) .................. 10 2004 058 081
Sep. 24, 2005   (DE) .................. 20 2005 015 106 U

(51) Int. Cl.
*A61F 13/00*    (2006.01)
*A61C 3/00*     (2006.01)
(52) U.S. Cl. .......................... 128/848; 433/6
(58) Field of Classification Search .......... 128/848, 128/859–862; 433/6
See application file for complete search history.

(56) References Cited

U.S. PATENT DOCUMENTS

| 5,267,862 A | 12/1993 | Parker |
| 5,462,066 A | 10/1995 | Snyder |
| 5,499,633 A | 3/1996 | Fenton |
| 5,829,441 A * | 11/1998 | Kidd et al. .................. 128/848 |
| 5,868,138 A | 2/1999 | Halstrom |
| 6,055,986 A * | 5/2000 | Meade .................. 128/848 |
| 6,099,304 A * | 8/2000 | Carter .................. 433/19 |
| 6,161,542 A | 12/2000 | Halstrom |
| 6,305,376 B1 | 10/2001 | Thornton |
| 6,729,335 B1 | 5/2004 | Halstrom |
| 2002/0000230 A1 * | 1/2002 | Gaskell .................. 128/848 |
| 2003/0217753 A1 | 11/2003 | Thornton |
| 2007/0074729 A1 * | 4/2007 | Magnin .................. 128/859 |

FOREIGN PATENT DOCUMENTS

| EP | 0 359 135 | 3/1990 |
| EP | 0 801 937 | 10/1997 |
| EP | 1 203 570 | 5/2002 |

* cited by examiner

*Primary Examiner*—Patricia M Bianco
*Assistant Examiner*—Tarla R Patel
(74) *Attorney, Agent, or Firm*—Davis & Bujold, P.L.L.C.

(57) ABSTRACT

The invention relates to a two-part mandibular protrusion splint (1) for preventing snoring and/or obstructive sleep apnoea, comprising a lower part (2) and an upper part (3), comprising shaping and flexurally rigid trays (2a, 3a) which are open towards the mandibula and maxilla respectively, where the bottom surfaces of the outsides of the two trays (2a, 3a) are connected to one another in such a way that they are continuously adjustable relative to one another in the longitudinal direction, and a corresponding ready-to-use set for the production or restoration of mandibular protrusion splints consisting of (i) shaping and flexurally rigid trays (2a, 3a) with preformed attachment elements on the outsides of each of the bottom surfaces; (ii) one or more adjustment screws (10) for connecting the attachment elements; and (iii) optionally use instructions.

25 Claims, 8 Drawing Sheets

CONTINUOUSLY ADJUSTABLE MANDIBULAR PROTRUSION SPLINT FOR TREATING SNORING AND OBSTRUCTIVE SLEEP APNEA

BACKGROUND OF THE INVENTION

1. Technical Field

The invention relates to a continuously adjustable, two-part mandibular protrusion splint for treating snoring and/or obstructive sleep apnea.

2. Prior Art

Snoring may be a symptom of obstructive sleep apnea syndrome, characterized by repeated and frequent cessation of breathing at night, which may be associated with severe health complications, such as, for example, high blood pressure, cardiovascular diseases, strokes, inter alia. U.S. Pat. No. 5,462,066 and European patent application EP 1 203 570 have disclosed brace-like bite splints of this type for preventing snoring, which serve to move the mandibula slightly forwards, since in this position of the mandibula the respiratory tracts are opened wider, enabling the patient to breathe more freely without snoring.

The known bite splints in the form of a one-piece, brace-like mouthpiece consist of thermoplastic materials having two bite channels, which are shapeable on warming. The patient puts the warmed, as yet unfitted mouthpiece in the mouth and then presses the mandibular and maxillar teeth into the corresponding lower and upper bite channels in the shapeable plastic and fits them to the bite channels by biting on the bite plates. The plastic cools in the process and regains its solid elasticity, after which the mouthpiece has been fitted to the patient. During the fitting operation, it must be ensured that the mandibula is moved forwards somewhat in order to establish a permanent protrusion. The known bite splints have the disadvantage that a protrusion, once established, can only be adapted with difficulty to changing needs of the patient, and consequently the effect achieved initially deteriorates with time.

Furthermore, U.S. Pat. No. 5,868,138 proposes a dental appliance for treating snoring and obstructive sleep apnea which has a maxillar part, a mandibular part and a connecting means, where the connecting means retains the lower part in an adjustable manner in an anterior, protruded position relative to the upper part.

To this end, maxillar and mandibular splints have to be manufactured individually in the dental laboratory after an impression has been taken.

The connecting means proposed, which generally consists of the material titanium, is a pin which is attached in a fixed manner perpendicular to the base surface of the upper part and can be coupled in a stepwise manner in various positions of the lower part.

The present invention was based on the object of providing snorers and sleep apnea sufferers, by comparison, with a mandibular protrusion splint with comparable efficacy which has a long service life and is easy to handle. In addition, the splint to be developed should be capable of being fitted easily by any doctor—not only by dentists—or even by the patient themselves, which requires a considerable simplification in handling. Furthermore, the mandibular protrusion of the mandibular protrusion splint according to the invention should be capable of being matched steplessly to the needs of the patient.

This object has been achieved in accordance with the invention by the provision of a universal two-part mandibular protrusion splint comprising a lower part (2) and an upper part (3), each of are shaped in the manner of a dental brace to fit the human maxilla and mandibula, where the upper part is connected to the lower part via a connecting means arranged horizontally on the base surface of the two parts, in such a way that the lower part is adjustable continuously to the anterior in the longitudinal direction.

BRIEF SUMMARY OF THE INVENTION

The invention thus relates to a two-part mandibular protrusion splint (1) which can be employed universally for preventing snoring and/or obstructive sleep apnea, comprising a lower part (2) and an upper part (3), comprising shaping and flexurally rigid trays (2a, 3a) which are open towards the mandibula and maxilla respectively, where the outside of the bottom surface (2b) of the mandibular tray (2a) has in the center a screw guide (8) having a thread running parallel to the bottom surface (2b), and the outside of the bottom surfaces (3b) of the maxillar tray (3a) has in the center a guide rail (7) which is open towards the front for accommodation of the screw head of an adjustment screw (10) located in the thread, enabling the outsides of the two trays (2a, 3a) to be connected to one another in such a way that they are continuously adjustable in the longitudinal direction relative to one another.

In a first, universal embodiment, the shaping and flexurally rigid trays (2a, 3a) contain a thermoplastic filling material (4, 5) which can be shaped in the manner of a dental brace to fit the human maxilla and mandibula.

This embodiment avoids the time-consuming and expensive individual manufacture in the dental laboratory after prior taking of a dental impression by a dentist or orthodontist. In addition, this universal splint can easily be fitted by any doctor—not only by dentists—or even by the patient themselves, which requires a considerable simplification in handling.

In a further individual embodiment, the shaping and flexurally rigid trays (2a, 3a) are produced individually in the dental laboratory with an accurate fit, matched to the patient's dental and jaw conditions, from commercially available thermoforming discs (for example Erkoloc Pro thermoforming discs from Erkodent GmbH, Duran thermoforming discs from Scheu Dental GmbH, and many others) by the so-called pressure forming process after a dental impression has been taken. In this individual embodiment, the separate connecting element (50), consisting of the guide rail and the screw guide, is attached to the upper splint (guide rail) and lower splint (screw guide) in the dental laboratory.

The universal invention furthermore relates to a process for the production of a mandibular protrusion splint according to the invention, comprising the steps of:

(a) shaping of the shaping and flexurally rigid trays (2a, 3a) with attachment elements preformed on the outsides of each of the bottom surfaces by injection moulding;

(b) filling of the trays with a thermoplastic filling material (4, 5), preferably by injection moulding, in particular in the case of mass production; and (c) connection of the preformed attachment elements.

The universal invention furthermore relates to a process for the production of an individually fitted mandibular protrusion splint according to the invention, comprising the steps of:

(i) preparation of a dental splint on the basis of a dental impression from the patient;

(ii) attachment of a guide rail open towards the front to the underside of the maxillar splint;

(iii) attachment of a screw guide to the underside of the mandibular splint; and (iv) connection of the screw guide to the guide rail by means of a screw, whose head is accommodated by the guide rail.

The invention furthermore relates to the use of the two-part mandibular protrusion splint (1) according to the invention for the production of an appliance for preventing snoring and/or obstructive sleep apnea.

The invention furthermore relates to a ready-to-use set for the production of an appliance for preventing snoring and/or (obstructive) sleep apnea, consisting of:

(A) a lower part (2) and an upper part (3), comprising a shaping and flexurally rigid tray (2a, 3a) which is open towards the mandibula and maxilla respectively, where the outside of the bottom surface of the mandibular tray (2a) has in the center a screw guide (8) having a thread running parallel to the bottom surface, and the outside of the bottom surfaces of the maxillar tray (3a) has in the center a guide rail (7) which is open towards the front for accommodation of the screw head of an adjustment screw (10), and (B) two or more adjustment screws (10) of different length.

The invention furthermore relates to a ready-to-use set for the production of an appliance for preventing snoring and/or (obstructive) sleep apnea, consisting of:

(A) one or more two-part mandibular protrusion splints (1) according to the invention;

(B) an adapter (14) for the upper part of the two-part mandibular protrusion splint, which is designed in size and shape in such a way that it supports the outside of the bottom surface of the maxillar tray (3a) and having a device (14a) mounted on its surface which engages in the guide rail (7), open towards the front, of the maxillar tray (3a); and (C) optionally use instructions, in which the shaping, adjustment and cleaning of the two-part mandibular protrusion splint are explained.

The universal mandibular protrusion splint according to the invention has the advantage that it very firmly sits on or adheres to the two jaws, in a comparable manner to a dental splint, since, owing to the material nature of the thermoplastic splint filling, a very deep and uniform impression of all teeth is easily achieved. The firm seating is also favoured by the firm gripping of the thermoplastic by the solid outside walls of a flexurally rigid material consisting, for example, of polycarbonate. The mandibular protrusion splint furthermore has the advantage that it can be fitted by any doctor or even by the patient themselves within a few minutes in an uncomplicated manner without special aids. For this reason, a universal standard splint is also sufficient to fit virtually all jaw shapes. Furthermore, individual continuous adjustment of the mandibular protrusion is possible in an extremely advantageous manner. The special design of the splint means that it is very compact and after fitting the separation of the upper and lower anterior teeth of less than 10 mm is only very small, which has a very positive effect on wearing comfort and acceptance and also means that the splint is simultaneously suitable for jaw formations of different sizes.

DETAILED DESCRIPTION OF THE INVENTION

Figure 1:
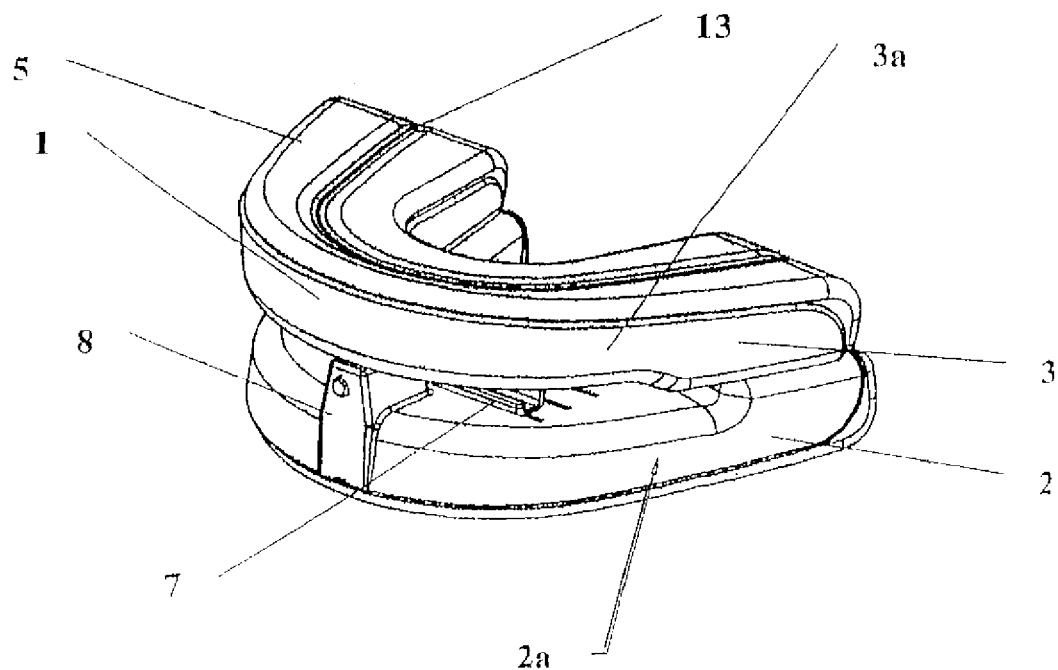
FIG. 1 shows a perspective view at an angle from the top and anterior of an embodiment of the universal protrusion splint according to the invention.

The protrusion splint according to the invention can either be universally mass-produced by injection moulding from known materials or produced in an individual variant by attachment of a suitable connecting element to the maxillar and mandibular trays manufactured in the dental laboratory.

The term "protrusion splint" or "mandibular protrusion splint" as used above and below denotes a dental appliance which allows the mandibula to be moved into a slightly anterior position compared with the maxilla and thus allows the cross section of the upper respiratory tracts to be increased. This results in a reduction in snoring and pauses in breathing as a consequence of obstructive sleep apnea.

The term "thermoplastic filling material" as used above and below denotes a material which can be deformed plastically at elevated temperature, preferably below 60° C., preferably between 40 and 50° C., and comes into close contact with a pre-specified mould and then retains this said shape on cooling. Suitable materials are polymers and copolymers or mixtures thereof from the group of the polyethylenes (PE), polyvinyl acetates (PVA), acrylates and methacrylates, preferably copolymers of PE and PVA, as available, for example, from DuPont under the trade name Elvax®. Preference is given to PE-PVA copolymers whose PVA content is from 20 to 40%, in particular 25 to 35%.

The term "shaping and flexurally rigid tray" as used above and below denotes both a "U- or horseshoe-shaped" moulding which forms a tray or trough which is open or closed at the ends, and also an upper or lower part of a dental splint produced by individual fitting. In general, this moulding consists of a material which is inert and stable under physiological conditions, such as, for example, thermosetting plastics, such as, for example, polytetrafluoroethylene (PTFE, Teflon®), or polycarbonates or of elastomers, such as, for example, polyacrylates.

The term "a guide rail which is open towards the front" as used above and below denotes a "C rail", which surrounds the screw head and prevents loosening of the connection between adjustment screw and the screw guide of the lower tray to the anterior in the longitudinal direction, but allows lateral movements of the mandibula. This "C rail" is open at the two lateral ends, so that the head of the adjustment screw can easily be inserted from the side.

In general, the "C rail" consists of the same material as the flexurally stable tray and is firmly connected to the underside of the tray or it consists in the individual variant of an inert, stable metal and is located on a baseplate of metal, which preferably has one or more cut-outs. This embodiment is particularly suitable for embedding in a dental splint produced individually on the basis of an impression of the bite of the patient.

The term "adjustment screw" as used above and below denotes a stepless connecting element which is adjustable continuously in the screw guide (8) parallel to the bottom part of the lower part. The screw head itself sits virtually immovably firmly in the "C rail". In general, this adjustment screw consists of a material which is inert and stable under physiological conditions, such as, for example, metals, such as titanium or stainless steel, ceramic materials or thermosetting plastics.

In general, the "screw guide" consists of the same material as the flexurally stable tray and is firmly connected to the underside of the tray or it consists in the individual embodiment of an inert, stable metal and is located on a baseplate of metal, which has one or more cut-outs. This embodiment is particularly suitable for embedding in a dental splint produced individually on the basis of an impression of the bite of the patient.

The information used above and below with respect to the geometry or spatial arrangement of the protrusion splint or of parts thereof depends on the circumstances of the protrusion splint in its use as intended, i.e. after placing thereof onto the upper and lower dentition of the person in question: "in the longitudinal direction" means in the direction of the mouth opening ("anterior") or throat ("posterior"); "to the front" (anterior) means in the direction of the mouth opening; "in the center" means in the region of the incisor teeth; "at the back" means in the region of the molar teeth.

Advantageous embodiments of the invention are universal mandibular protrusion splints in which (a) the filling material (4, 5) consists of one or more copolymers of polyethylene and polyvinyl acetate, in particular in which the filling material consists of a thermoplastic copolymer or a mixture of two or more thermoplastic copolymers which themselves consist of polyethylene and polyvinyl acetate, and the softening point of the resultant plastic is at a temperature of 40 to 50° C., preferably at about 44° C.;

(b) an orientation channel (13) is shaped into the filling material (4) of the upper tray for accommodation of the teeth;

(c) the shaping and flexurally rigid tray (2a, 3a) consists of polycarbonate;

(d) the separation between the inside bottom of the maxillar tray and the inside bottom of the mandibular tray, in the assembled state, is less than 10 mm, preferably from 6 to 9 mm, in particular about 8 mm; a separation of the teeth in the anterior tooth region of about 8.0 to 8.4 mm with the splint in place is particularly preferably achieved. In general, this results in easier and more complete closing of the mouth, even in the case of small jaw sizes, without muscle strain. This results in higher wearing comfort and thus also better acceptance (compliance).

(e) their height in the assembled state is less than 30 mm, preferably from 20 to 28 mm, in particular about 27 mm;

(f) their total length, i.e. the separation between the frontmost part and the center formed by the two arms, in the assembled state is less than 50 mm, preferably from 42 to 48 mm, in particular about 45 mm;

(g) the two trays (2a, 3a) are connected to one another in such a way that they are adjustable continuously in the longitudinal direction relative to one another by up to 14 mm, preferably >0 to 12 mm. The mandibular protrusion splint together with at least three adjustment screws is particularly preferably made available in different lengths, with one adjustment screw preferably having a length of up to 14 mm, in particular about 12 mm, and the other adjustment screw having a length of up to 18 mm, in particular about 16 mm, and a third adjustment screw having a length of up to 22 mm, in particular about 20 mm.

The production of the universal mandibular protrusion splint according to the invention is simple per se:

(a) the shaping and flexurally rigid trays (2a, 3a) with attachment elements preformed on the outsides of each of the bottom surfaces are shaped by injection moulding;

(b) the trays are filled with a thermoplastic filling material (4, 5), likewise by injection moulding in the case of mass production or in particular individual cases also manually; and (c) the preformed attachment elements are connected.

The copolymer used, apart from the conventional mass production by injection moulding, can also in particular individual cases be shaped manually after heating in granule form in a water bath to give a homogeneous plastic material and then pressed into empty unfilled trays. If these trays with their filling are subsequently heated in hot, preferably boiling water for about 2 to 4 minutes and, after brief cooling, the plastic material is uniformly distributed in the trays and then allowed to harden, a fully functioning mandibular protrusion splint according to the invention can thus be produced. The polymeric material adheres absolutely firmly to the contact surface of polycarbonate. If a doctor or patient should be unsuccessful in fitting at the first attempt due to biting in the wrong place, the splint can be restored to the new state again very simply in this manner.

If the adhesion of the splint to teeth and jaws should furthermore lessen after a long wearing time over many months, the original splint filling can thus likewise easily be fully restored and the fitting then carried out again. The mandibular protrusion splint according to the invention can thus be used over a very long period after any interim repairs. The invention thus furthermore relates to a set for the production or restoration of a mandibular protrusion splint according to the invention, essentially consisting of (i) the shaping and flexurally rigid trays (2a, 3a) with preformed attachment elements on the outsides of each of the bottom surfaces;

(ii) a plastic component which is suitable for the production of the thermoplastic filling (4, 5);

(iii) one or more adjustment screws (10) for connecting the attachment elements; and (iv) use instructions for the production or restoration of a mandibular protrusion splint according to the invention;

where component (ii) comprises more than the amount of plastic required for the production of the mandibular protrusion splint according to the invention.

Furthermore, a connecting element consisting of a "C rail" and a screw guide made of stainless steel or a physiologically inert metal, such as, for example, titanium, can be attached in a manner known per se on the basis of a dental impression from the patient to a dental splint manufactured individually in the dental laboratory to the undersides of both upper and lower trays.

This embodiment can be produced by manufacturing a dental splint in a manner known per se starting from a bite impression of the maxilla and mandibula of a patient, preferably in a dental laboratory. Alginate impressions are taken by a dentist, and the mandibular protrusion is prespecified from this (taking of a so-called construction bite using a bite fork in order to fix a slight protrusion of the mandibula).

A plaster model is then constructed in the dental laboratory and articulated in with the aid of protrusion bite registration. After model duplication, hard-elastic trays for maxilla and mandibula are thermoformed with the aid of the pressure forming technique as the basis for the construction of the individual mandibular protrusion splint. The production process can be carried out using all common commercially available thermoforming discs in various thicknesses, for example Erkoloc Pro (Erkodent GmbH) in a thickness of 2 to 3 mm, Duran (Scheu Dental GmbH) in a thickness of 2.0 mm, and many others. The thermoforming process can likewise be carried out using standard commercial equipment, such as, for example, the BIOSTAR® or MINISTAR® units from Scheu Dental GmbH or ERKOPRESS® from Erkodent GmbH.

After the thermoformed trays for maxilla and mandibula have cooled, acrylic resin can be distributed on the surface. This makes the thermoformed trays stronger and enables them to be treated (polished) better. In general, no acrylate is applied in the anterior tooth region. The cooled raw mould is then removed from the model, cut to size and polished.

An acrylate adhesive is subsequently applied to the points in the anterior tooth region where the connecting element is to be fixed. The lower baseplate with the screw guide is fixed to the underside of the mandibular splint using acrylate adhesive, and the attachment holes of the baseplate are covered with clear, cold-polymerizing plastic. Plastic can be applied in the region of the 6th and 7th teeth in order—if specified by the dentist—to ensure distal support.

The upper baseplate with the "C rail" is fixed in the anterior tooth region of the maxillar splint using acrylate adhesive by the same process.

After curing of the acrylate adhesive, the splints are ground and polished. The two trays for maxilla and mandibula can then be connected to one another via an adjustment screw.

The screw guide and the "C rail" are produced in a manner known per se. Either the corresponding mouldings can be milled from a block of material, produced by moulding techniques, shaped from plates or sheets, if necessary with warming, produced by welding or soldering, in particular by laser welding of a plurality of prefabricated components, in particular from a baseplate with a "C rail" or a baseplate with a screw collar or screw bush, or, if they consist of thermosets, also by injection moulding.

The invention thus furthermore relates to a ready-to-use set for the production of a connecting element for a mandibular protrusion splint according to the invention, essentially consisting of (A) a moulding consisting of a "C rail" (7) and a baseplate (51) arranged perpendicular thereto;

(B) a moulding consisting of a screw guide and a baseplate (52) arranged perpendicular thereto, where the two baseplates (51, 52) are matched to the bottom surfaces of the flexurally rigid trays (2a, 3a) of the mandibular protrusion splint and have one or more cut-outs (53); and (C) one or more adjustment screws, if desired of different length, for connecting the "C rail" (7) to the screw guide (8), where the screw head is accommodated by the "C rail" and the screw thread fits the internal thread of the screw guide.

Illustrative embodiments of the invention are shown in the drawings and are described in greater detail below.

FIG. 1 shows a perspective view at an angle from the top and anterior of an embodiment of the universal protrusion splint (1) according to the invention formed from a lower part (2) and an upper part (3), each of which is formed from a tray (2a, 3a) and a filling material (4, 5). The filling material (4) of the lower part cannot be seen in FIG. 1, but the channel (13) in the filling material (5) of the upper part, which serves for better orientation of the teeth on insertion of the protrusion splint, is clearly evident. Furthermore, the lower part (2) of the protrusion splint (1) has in the anterior region a screw guide (8) having a thread (9) for accommodation of an adjustment screw, which is not evident in FIG. 1, the head of which engages in the guide rail ("C rail") (7).

Figure 2:
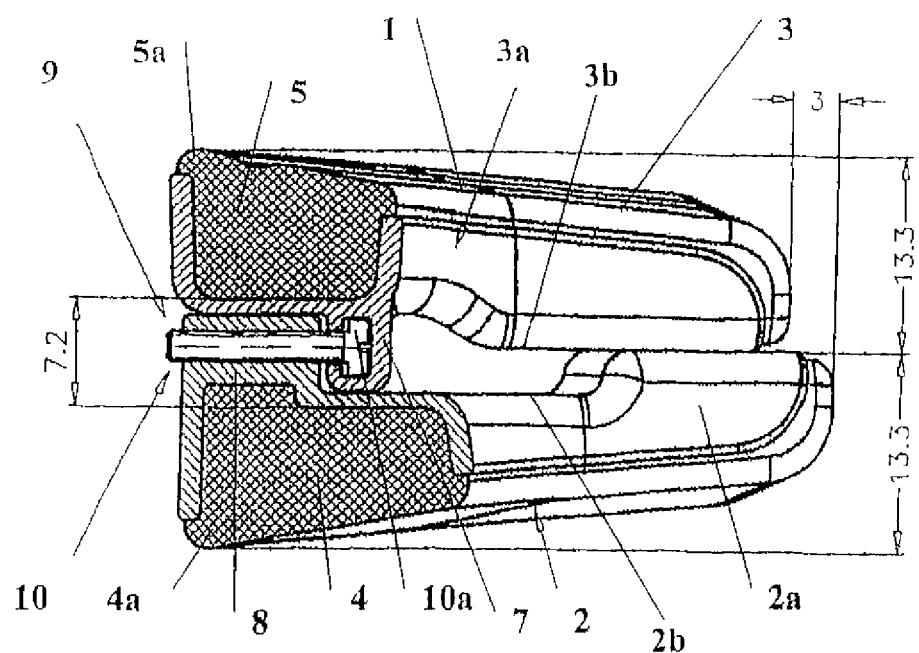
FIG. 2 shows a longitudinal section through this protrusion splint along the adjustment screw.
Figure 3:
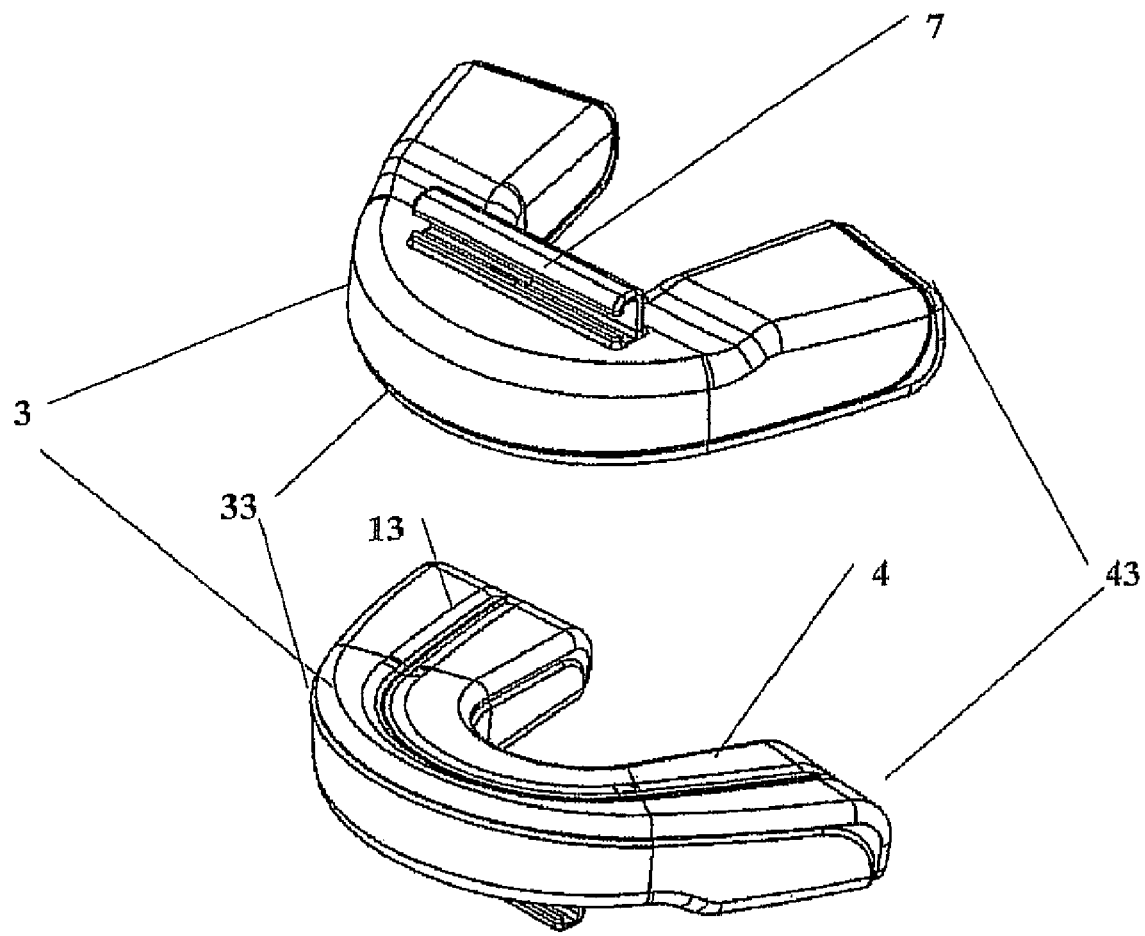
FIG. 3 shows a perspective view of the upper part, in each case at an angle from the top and bottom.
Figure 4:
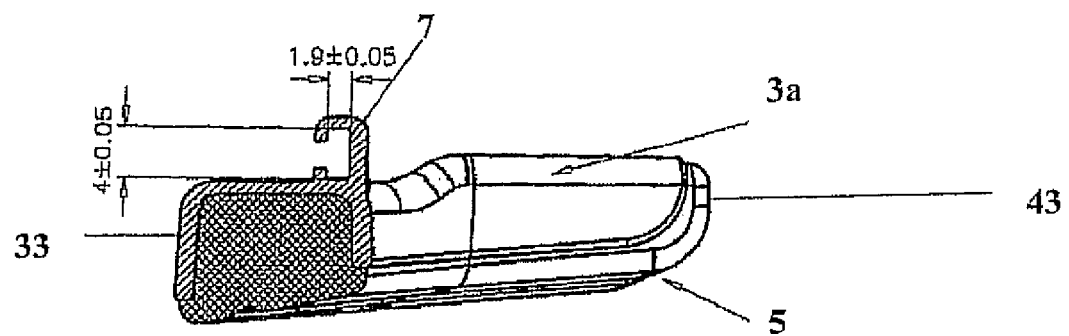
FIG. 4 shows a longitudinal section through the upper part.
Figure 5:
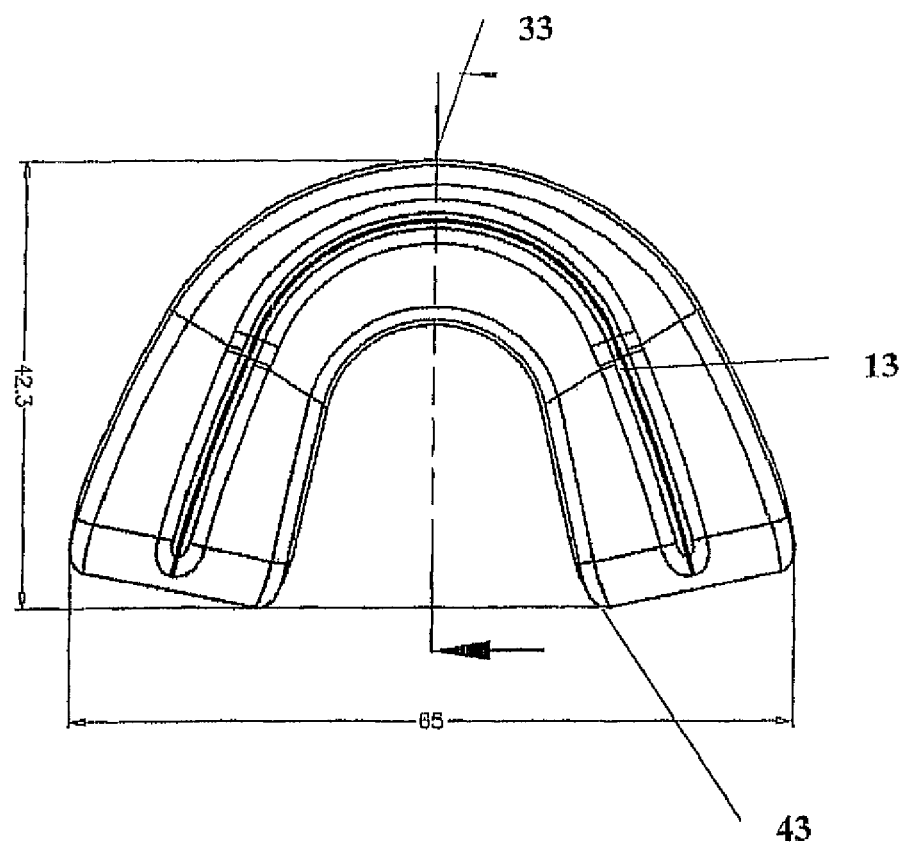
FIG. 5 shows a plan view of the upper part from the top.
Figure 6:
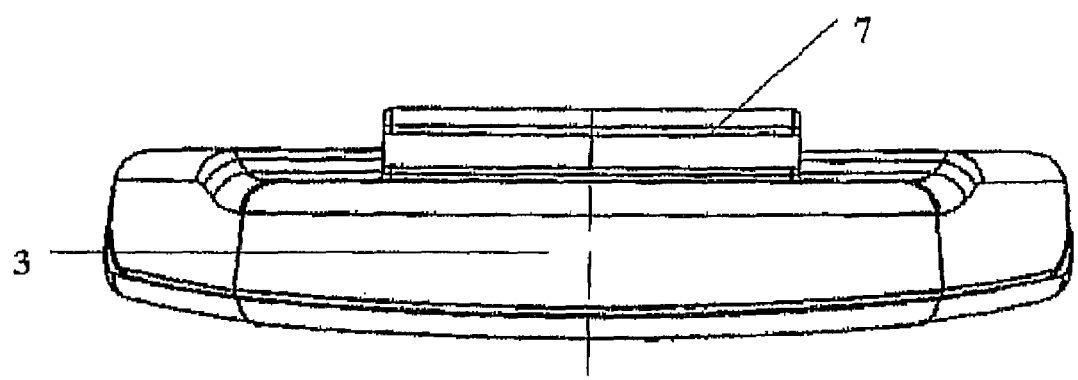
FIG. 6 shows an anterior view of the upper part.
Figure 7:
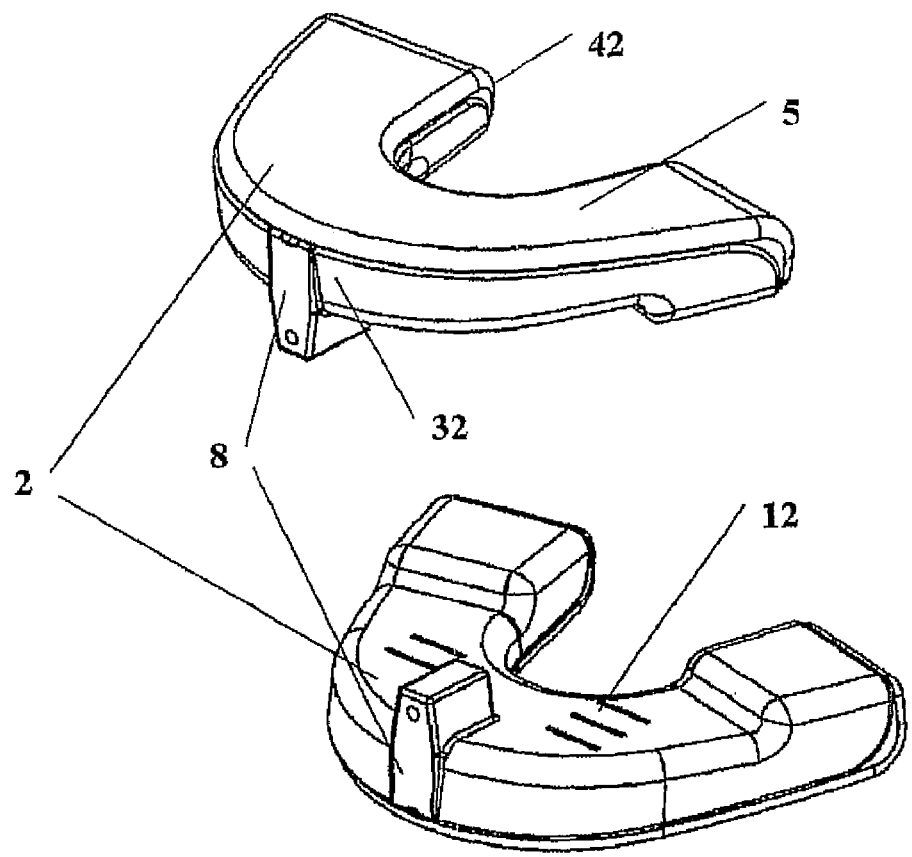
FIG. 7 shows a perspective view of the lower part, in each case at an angle from the top and bottom.
Figure 8:
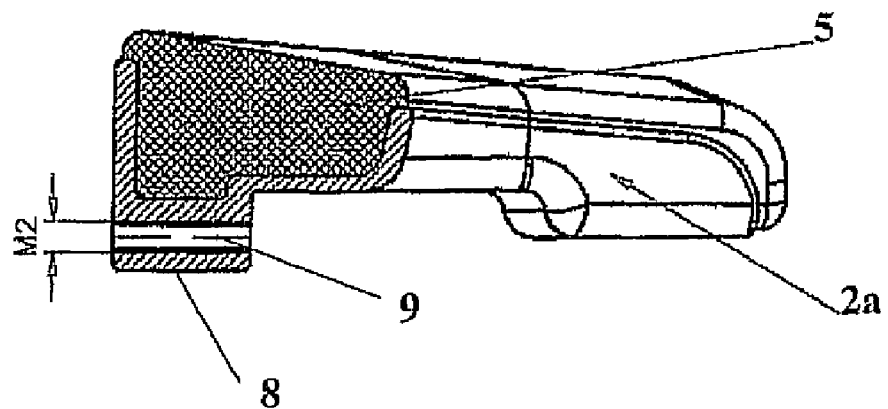
FIG. 8 shows a longitudinal section through the lower part

FIG. 2 shows a longitudinal section through this protrusion splint (1) along the adjustment screw (10) formed from a lower part (2) and an upper part (3), each of which is formed from a tray (2a, 3a) and a filling material (4, 5). As is evident from FIGS. 2, 4 and 8, the thermoplastic material (4, 5) in each case projects beyond the height of the flexurally rigid trays, preferably by 0.5 to 3 mm, in particular by 1 to 1.5 mm (4a, 5a). This results in increased adhesion of the teeth and at the same time in protection of the gums from injury by the edges of the flexurally rigid trays.

The adjustment screw (10) in the fully screwed-in state is located in the screw guide (8), its head (10a) is surrounded by the "C rail" (7).

It is furthermore clearly evident that the outside walls (32, 33) of the two trays in the anterior region are higher than the respective inside walls (42, 43). The anterior delimitation of the screw guide (8) is flush with the outside wall (42) of the lower part. The length of the thread in the screw guide (8) is 6 to 12 mm, preferably 8 to 10 mm, in particular about 9 mm.

The separation between the inside bottoms of the two trays in the anterior tooth region ("tooth separation") is less than 10 mm, preferably 6 to 9 mm, in particular about 8 mm. In the region of the incisor teeth, the protrusion splint before fitting to the bite has a total height of less than 30 mm, preferably 24 to 28 mm, in particular about 26.5 mm.

The detail views of the upper part (3) depicted in FIGS. 3 to 6 illustrate the structure and function of this part of the protrusion splint according to the invention. The length of the guide rail (7) open towards the front is less than 35 mm, preferably 26 to 30 mm, in particular 28 mm.

The length of the guide rail allows lateral movement of the mandibula without the connection of the two parts becoming loosened.

The separation of the two outside walls at the posterior end of the upper part (maximum width of the mandibular splint) is 60 to 70 mm, preferably 62 to 68 mm, in particular about 65 mm. The separation between the outside wall (33) in the region of the incisor teeth and an imaginary line between the posterior ends of the inside wall (43) (maximum length of the mandibular splint) is 43 to 46 mm, in particular about 44.3 mm (cf. FIG. 9). The total height of the guide rail (7) is 5 to 7 mm, in particular about 6 mm. The internal width of the guide rail is 3.8 to 7.2 mm, in particular about 4 mm. The inside depth of the guide rail is 1.8 to 2.0 mm, in particular about 1.9 mm. In order to produce the flexurally stable upper tray (3a), 3.0 to 4.0 cm$^3$ of polycarbonate are used.

In order to produce the filling of the upper tray, 10.0 to 12.0 cm$^3$ of a copolymer of PE and PVA are used.

The detail views of the lower part (2) depicted in FIGS. 7 to 10 illustrate the structure and function of this part of the protrusion splint according to the invention. The width of the screw guide (8) perpendicular to the direction of the thread is 4 to 9 mm, in particular about 6 mm. The length of the screw guide (8) parallel to the direction of the thread is 7 to 11 mm, in particular about 9 mm. The height of the screw guide (8) is 4 to 6 mm, in particular about 5 mm.

The stated length, width and height of the screw guide (8) enable secure retention of the adjustment screw in the thread and in addition permit a small separation to be set between the incisor teeth of the maxilla and mandibular which results in increased wearing comfort and better acceptance.

The separation of the two outside walls at the posterior end of the lower part (maximum width of the maxillar splint) is 60 to 70 mm, preferably 62 to 68 mm, in particular about 65 mm. The separation between the outside wall (32) in the region of the incisor teeth and an imaginary line between the posterior ends of the inside wall (42) (maximum length of the maxillar splint) is 40 to 44 mm, in particular about 42.5 mm. In order to produce the flexurally stable lower tray, 2.5 to 3.5 cm$^3$ of polycarbonate were used. In order to produce the filling of the lower tray (2a) 10.0 to 12.0 cm$^3$ of a copolymer of PE and PVA were used.

Figure 9:
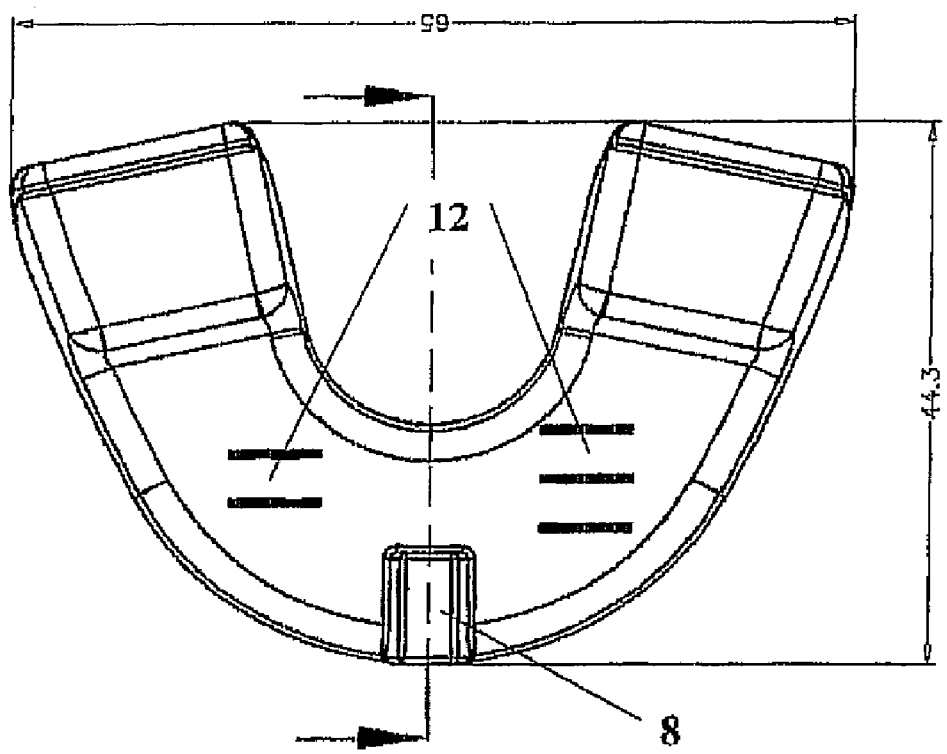
FIG. 9 shows a plan view of the lower part from the top.
Figure 10:
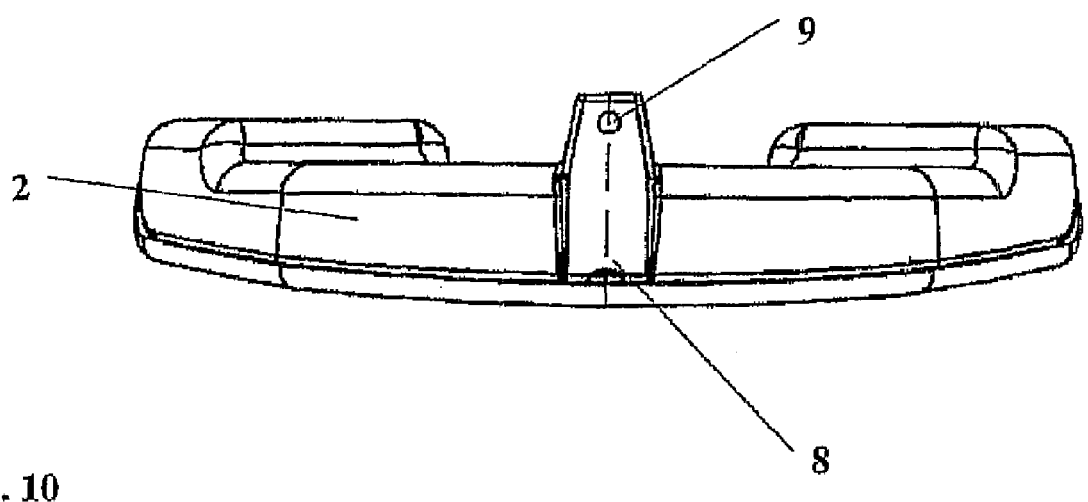
FIG. 10 shows an anterior view of the lower part.

FIG. 9 shows respectively two and three straight lines to the right and left of the screw guide (8). These serve as a scale (12) in order to ensure reproducible adjustment of the mandibular splint by means of the adjustment screw.

Fitting of the universal protrusion splint according to the invention to the jaw of the person in question is simple. The fitting can generally be carried out by any doctor in any specialism, their trained staff or usually also by the person in question alone with the aid of a mirror.

If tooth malpositions, anamnetic mandibular joint complaints or tooth diseases, such as, for example, parodontosis, inter alia, are present, it is advisable to consult a dentist before fitting.

During fitting of the universal splint, firstly the upper part (3) is warmed to a temperature above the softening point of the filling material (4), preferably in a water bath at a water temperature above 50° C. The upper part is then fitted to the dentition of the maxilla by pressing the teeth to a uniform depth into the soft, plastic and still-warm filling material. The filling material is subsequently allowed to cool briefly in the mouth for about 30-60 seconds and then finally hardened in a cold water bath.

Figure 11:
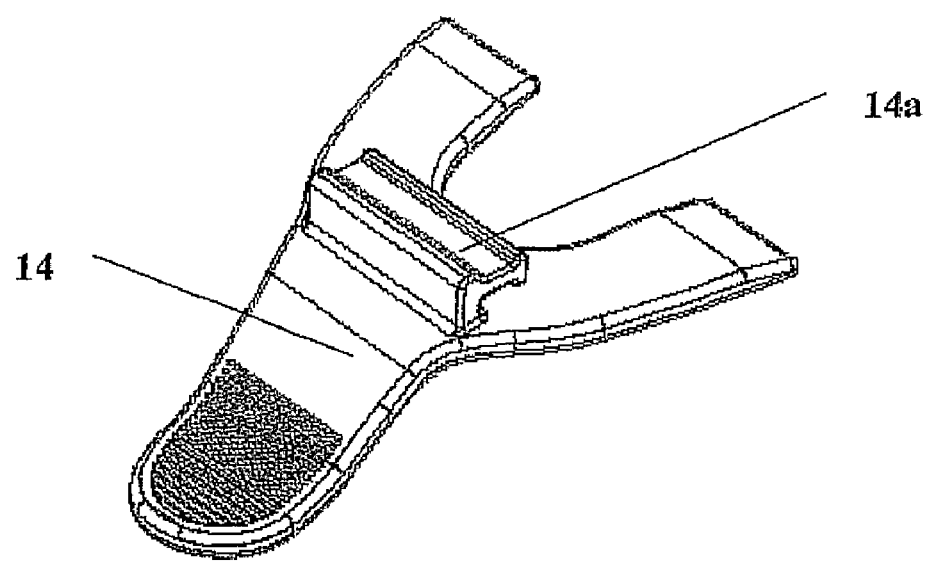
FIG. 11 shows a suitable adapter for the upper part.

Alternatively, the upper part (3) can be fitted using an adapter (14) shown in FIG. 11.

The lower part (2) is then warmed correspondingly and connected to the already fitted upper part with the aid of the adjustment screw, which is firstly screwed in as far as the stop as shown in FIG. 2 for the purposes of fitting, the shaped upper part is inserted into the maxilla, and the teeth of the mandibula are carefully pressed into the soft filling material (5) of the lower part. After hardening, the adjustment screw is turned into the suitable position for the particular person.

Figure 12:
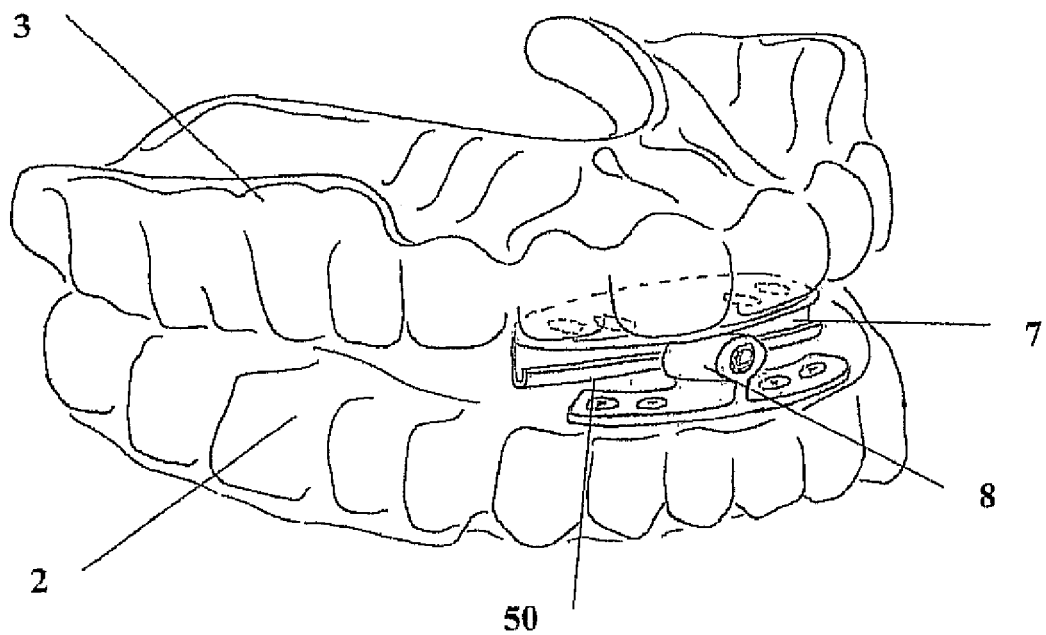
FIG. 12 shows a further embodiment of the individually fitted protrusion splint according to the invention from the anterior and side.

FIG. 12 shows a representation of a further embodiment of the protrusion splint (1), consisting of a lower part (2) and an upper part (3), which have been fitted individually to the mandibula and maxilla respectively of a patient and in which a connecting element (50) consisting of a "C rail" (7) and a screw guide (8) have subsequently been embedded.

In the screwed-in state, the adjustment screw (10) is located in the screw guide (8), its head (10a) is surrounded by the "C rail" (7). The protrusion can be fixed in a pre-specified position by an additional counternut.

Figure 13A:
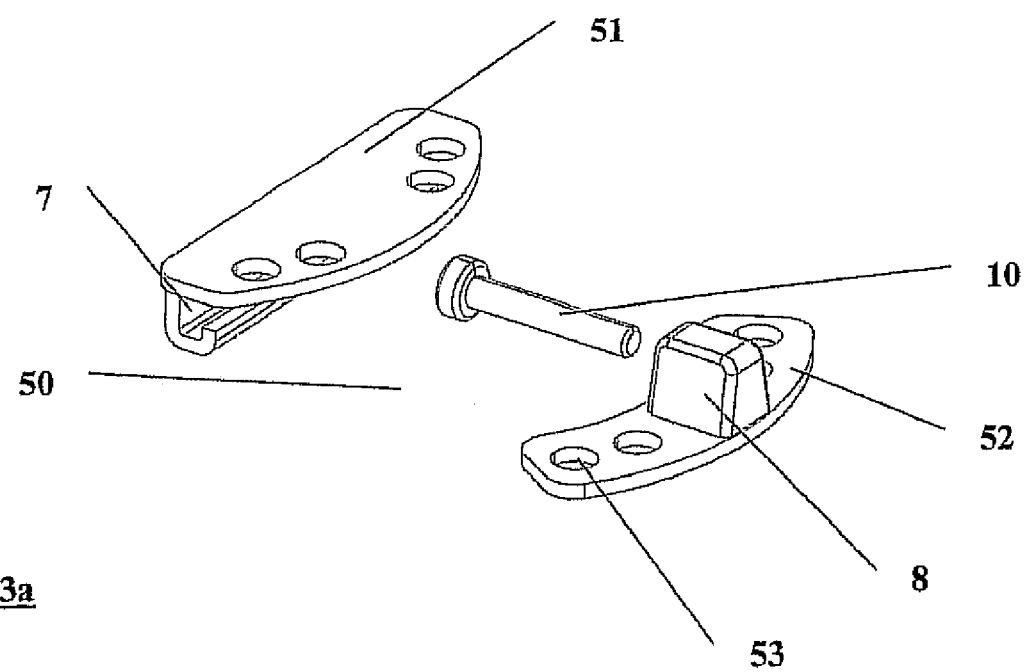
FIGS. 13a, 13b and 13c show alternative embodiments of connecting elements of the individually fitted protrusion splint.
Figure 13B:
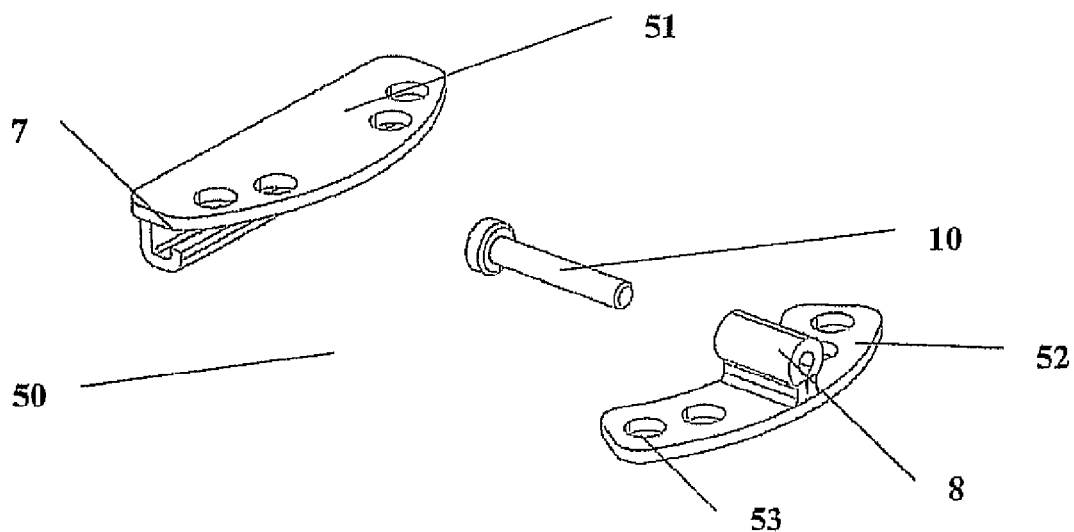
Figure 13C:
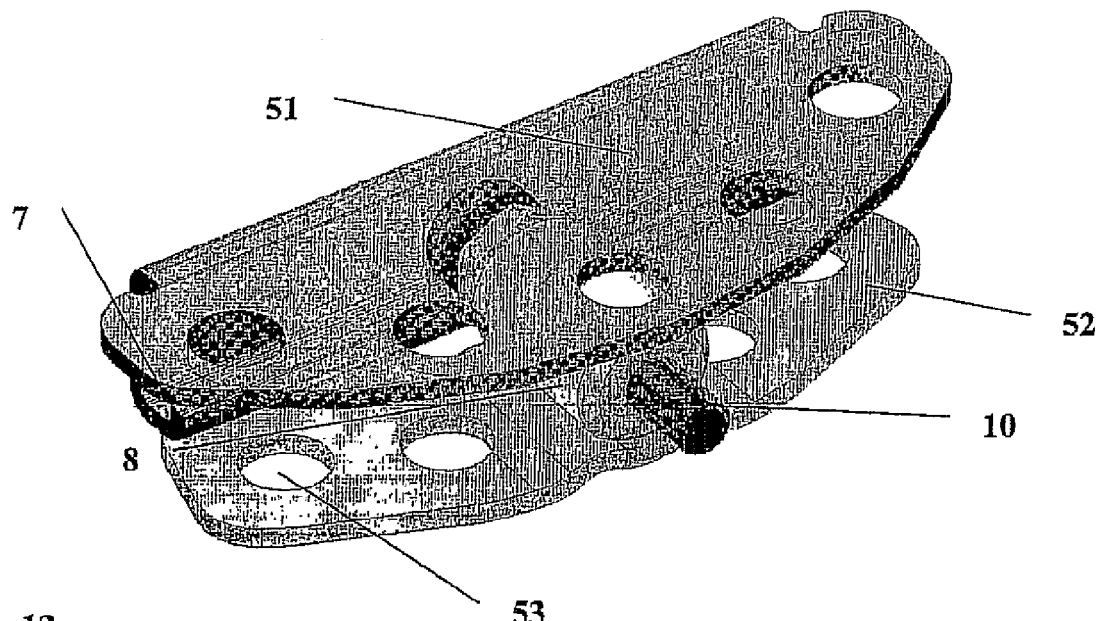

FIGS. 13a, 13b and 13c show details of alternative embodiments of the connecting elements (50) with a "C rail" (7) arranged perpendicular to a baseplate (51) and a screw guide (8) likewise arranged perpendicular to a baseplate (52). The shapes of the two baseplates are matched to the shape of the bottom surface of the respective tray to be connected to them and have one or more cut-outs (53). Whereas the individual components of the connecting elements of FIGS. 13a and 13b are shown separately, FIG. 13c shows a connecting element according to the invention in which the screw (10) is screwed to the screw guide (8) and the screw head engages in the "C rail" (7).

The connecting element in FIG. 13a has been produced by milling from two metal blocks. The connecting element in FIG. 13b has been obtained by bending and folding techniques from correspondingly pre-shaped metal sheets. In the case of the connecting element in FIG. 13c, in each case a "C rail" (7) and a screw bush (8) have been attached to the associated baseplate (51) and (52) respectively by laser welding.

The preferred dimensions of the guide rail (7) and the screw guide (8) indicated with respect to FIGS. 3 to 10 also apply to the guide rail (7) and screw guide (8) in FIGS. 12, 13a, 13b and 13c.

The universal mandibular protrusion splint according to the invention eliminates or reduces snoring and pauses in breathing as a consequence of obstructive sleep apnea. Due to its compact size, it has high wearing comfort. It provides a firm, sure hold for the enveloped teeth, can be matched steplessly to the needs of the patient with respect to the mandibular protrusion, protects the teeth against grinding of the teeth at night and protects the gums against injury.

The mandibular protrusion splint manufactured individually in the dental laboratory with the aid of the connecting elements is more filigree and less bulky owing to the very thin thermoforming discs. The patient's tongue therefore has more room in the oral cavity, which means improved wearing comfort compared with the universal splint. Depending on the durability of the thermoforming discs used, which is highly dependent on their chemical composition and thickness, the service life of the individual splint is longer than that of the universal splint. The individual protrusion splint therefore appears more suitable for long-term therapy lasting years compared with the universal, mass-produced and inexpensive splint. Since the effect and acceptance by the patient cannot be predicted for any mandibular protrusion splint, irrespective of the production process, the use of the less expensive universal splint as emergency care splint is always advisable at first for cost reasons. When the efficacy and acceptance by the patient have been demonstrated, the universal splint should then be replaced, for example after one to two years, by the individually manufactured mandibular protrusion splint for the purposes of long-term treatment.

The invention claimed is:

1. A two-part mandibular protrusion splint (1) for preventing at least one of snoring and obstructive sleep apnea, the two-part mandibular protrusion splint (1) comprising:
a lower part (2) comprising a shaping and flexurally rigid mandibular tray (2a) which is open towards a mandibula; and
an upper part (3) comprising a shaping and flexurally rigid maxillar tray (3a) which is open towards a maxilla;
wherein an outside of a bottom surface of the mandibular tray (2a) has a screw guide (8), having a thread running parallel to the bottom surface, in the center thereof, and an outside of a bottom surface of the maxillar tray (3a) has, in a center thereof, a guide rail (7) which is open towards a front for accommodation of the screw head of an adjustment screw (10) located in the thread, the screw head (10a) is surrounded by the guide rail which has a length that facilitates lateral movement of the mandibular without a connection between the screw head and the guide rail becoming loosened, enabling the rigid mandibular and maxillar two trays (2a, 3a) to be connected to one another in such a way that the rigid mandibular and maxillar two trays (2a, 3a) are continuously adjustable relative to one another in a longitudinal direction.

2. The mandibular protrusion splint according to claim 1, wherein the shaping and flexurally rigid mandibular and maxillar trays (2a, 3a) contain a thermoplastic filling material (4, 5) which, in each case, can be shaped in the manner of a dental brace to fit the human maxilla and mandibula.

3. The mandibular protrusion splint according to claim 2, wherein the filling material (4, 5) comprises at least one copolymer of polyethylene and polyvinyl acetate.

4. The mandibular protrusion splint according to claim 2, wherein the filling material (4, 5) comprises one of a thermoplastic copolymer and a mixture of at least two thermoplastic copolymers, where the copolymer comprises polyethylene and polyvinyl acetate, and a softening point (ASTM D 2240) of the mixture is at a temperature of 40 to 50° C.

5. The mandibular protrusion splint according to claim 1, wherein an orientation channel (13) is shaped into the filling material (4) of the maxillar tray in order to indicate a bite point for anterior teeth.

6. The mandibular protrusion splint according to claim 1, wherein the shaping and flexurally rigid mandillar and maxillar trays (2a, 3a) comprise polycarbonate.

7. The mandibular protrusion splint according to claim 1, wherein a separation, an assembled state, between the inside bottom of the maxillar tray (23) and the inside bottom of the mandibular tray (22) is less than 10 mm.

8. The mandibular protrusion splint according to claim 7, wherein the separation, in the assembled state, between the inside bottom of the maxillar tray (23) and the inside bottom of the mandibular tray (22) is between 6 and 9 mm.

9. The mandibular protrusion splint according to claim 8, wherein the separation, in the assembled state, between the inside bottom of the maxillar tray (23) and the inside bottom of the mandibular tray (22) is about 8 mm.

10. The mandibular protrusion splint according to claim 1, wherein, with the mandibular protrusion splint in place, a separation of teeth in an anterior tooth region is about 8.0 to 8.4 mm.

11. The mandibular protrusion splint according to claim 1, wherein a height of the mandibular protrusion splint, in an assembled state, is less than 30 mm.

12. The mandibular protrusion splint according to claim 11, wherein the height of the mandibular protrusion splint, in an assembled state, is between 20 and 28 mm.

13. The mandibular protrusion splint according to claim 12, wherein the height of the mandibular protrusion splint, in an assembled state, about 27 mm.

14. The mandibular protrusion splint according to claim 1, wherein a total length of the mandibular protrusion splint, in an assembled state, is less than 50 mm.

15. The mandibular protrusion splint according to claim 14, wherein the total length of the mandibular protrusion splint, in an assembled state, is from 42 to 48 mm.

16. The mandibular protrusion splint according to claim 15, wherein the total length of the mandibular protrusion splint, in an assembled state, is about 45 mm.

17. The mandibular protrusion splint according to claim 1, wherein the shaping and flexurally rigid mandibular and maxillar trays (2a, 3a) are connected to one another such that the shaping and flexurally rigid mandibular and maxillar trays (2a, 3a) are adjustable continuously in the longitudinal direction relative to one another by a distance of up to 14 mm.

18. The mandibular protrusion splint according to claim 17, wherein the shaping and flexurally rigid mandibular and maxillar trays (2a, 3a) are connected to one another in such a way that the shaping and flexurally rigid mandibular and maxillar trays (2a, 3a) are adjustable continuously in the longitudinal direction relative to one another by a distance of >0 to 12 mm.

19. The mandibular protrusion splint according to claim 1, wherein the underside of the lower shaping and flexurally rigid mandibular tray (2a) has a scale (12) for reproducible setting of the adjustment screw (10).

20. The mandibular protrusion splint according to claim 1, wherein the shaping and flexurally rigid mandibular and maxillar trays (2a, 3a) are produced with the aid of the pressure moulding technique from commercially available thermoforming discs of different chemical composition and thickness and are in each case shaped individually in the manner of a dental brace to fit the human maxilla and mandibula.

21. The mandibular protrusion splint according to claim 1, wherein the length of the guide rail (7) which is open towards the front and receives the screw head of the adjustment screw (10) is less than 35 mm.

22. The mandibular protrusion splint according to claim 1, wherein the length of the guide rail (7) which is open towards the front and receives the screw head of the adjustment screw (10) is 26 to 30 mm.

23. The mandibular protrusion splint according to claim 1, wherein the total height of the guide rail (7) which is open towards the front and receives the screw head of the adjustment screw (10) is 5 to 7 mm.

24. The mandibular protrusion splint according to claim 1, wherein the internal width of the guide rail (7) which is open towards the front and receives the screw head of an adjustment screw (10) is 3.8 to 7.2 mm.

25. A two-part mandibular protrusion splint (1) for preventing at least one of snoring and obstructive sleep apnea, the two-part mandibular protrusion splint (1) comprising:
a lower part (2) comprising a flexurally rigid arcuate mandibula tray (2a) which is open towards a mandibula of a user; and
an upper part (3) comprising a flexurally rigid arcuate maxilla tray (3a) which is open towards a maxilla of the user;
a first surface of the mandibular tray (2a) comprises a screw guide (8) with a thread directed parallel to the first surface of the mandibular tray (2a) in a center thereof;
an adjustment screw (10) is received in the thread and comprises a head (10a) that is directed to a rear of the mandibular tray (2a);
a first surface of the maxillar tray (3a) comprises a guide rail (7) which is open toward a front of the maxillar tray (3a) and is aligned with the screw guide, such that the guide rail (7) receives and engages a head (10a) of the adjustment screw (10), the guide rail (7) extends normal to the screw guide and facilitates laterally slidable engagement between the mandibular tray (2a) and the maxillar tray (3a), the adjustment screw (10) being rotatable within the thread to adjust spacing between the screw guide and the guide rail (7).

* * * * *